S. C. CARNEY
PROCESS FOR THE TREATMENT OF HYDROCARBONS
Dec. 9, 1930. Re. 17,898
Original Filed July 23, 1925
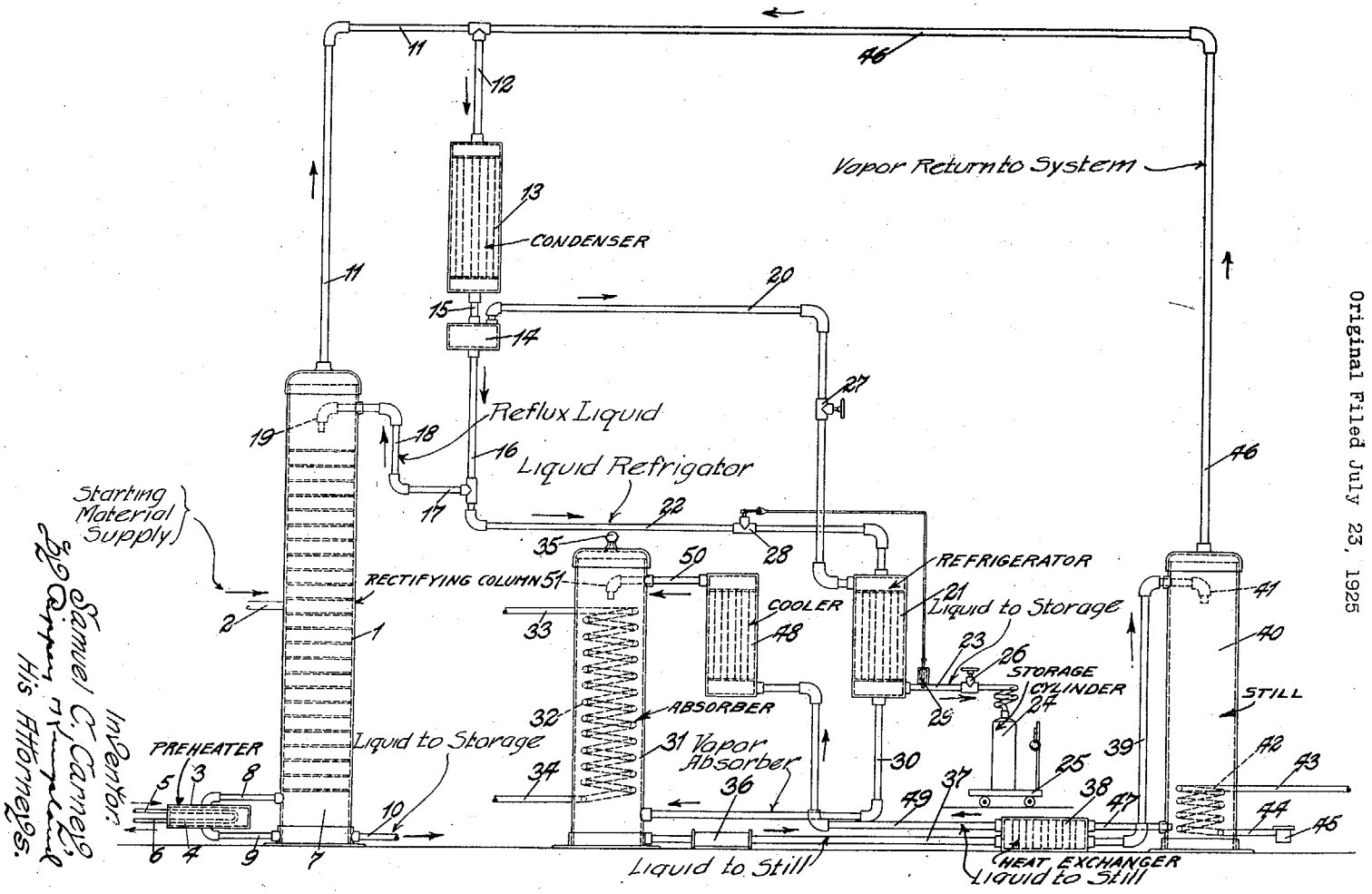
Inventor:
Samuel C. Carney,
By Rippey & Kingsland
His Attorneys.

Reissued Dec. 9, 1930

Re. 17,898

UNITED STATES PATENT OFFICE

SAMUEL C. CARNEY, OF SAN FRANCISCO, CALIFORNIA, ASSIGNOR TO SHELL PETROLEUM CORPORATION, A CORPORATION OF VIRGINIA

PROCESS FOR THE TREATMENT OF HYDROCARBONS

Original No. 1,768,827, dated July 1, 1930, Serial No. 45,661, filed July 23, 1925. Application for reissue filed October 18, 1930. Serial No. 490,559.

This invention relates to a new and useful process for the treatment of hydrocarbons.

An object of the invention is to recover in a liquid state highly volatile fractions of hydrocarbon mixtures, after the same have first been seperated from hydrocarbon mixtures having relatively high boiling points, by utilizing a part of the condensate resulting from the primary segregation of the heavier hydrocarbons as a refrigerant to reduce the temperature of the light fractions to a point at which they will condense under pressure.

Another object of the invention is to recover in a liquid state light fractions of hydrocarbon mixture and to withdraw and pack said liquefied light fractions under pressure, by subjecting hydrocarbon mixtures to an initial separation into a liquid and vaporous component; condensing a part of the vaporous component; then effecting a secondary separation of the condensate from the vapor, and then utilizing a part of the condensate in a refrigerating cycle to reduce the temperature of the vaporous component thereby condensing the same.

Additional objects of the invention will be apparent from the following detailed description thereof, taken in connection with the accompanying drawing in which a satisfactory form of apparatus for practicing the process is shown.

The mixtures to be treated are primarily segregated into a liquid component and a vaporous component, the liquid component being satisfactory for commercial purposes, and the vaporous component comprising the lighter fractions. The vaporous component thus separated from the liquid is in practice ordinarily that fraction of the original mixture which consists of hydrocarbons that have a boiling point below that of pentane. The vaporous segregated component, after the primary segregation from the heavier fraction of the original mixture, is subjected to a refrigerating cycle, in which a part of the liquefied component of the original mixture is utilized as the refrigerant. The result of the cooling effected by this refrigeration is to reduce the light fractions to a liquid form in which state it is drawn from the system, and may be stored in the usual containers for use as a refrigerant, or for other technical purposes.

It is known that certain characters of hydrocarbon mixtures may be initially segregated by treating the same in a rectifying column under the influence of heat and pressure coordinated to a degree sufficient to accomplish the initial segregation of the liquid component from the vapor. The vaporous component as a gas has very little technical value, but because of its low boiling point when liquefied it is highly satisfactory as a refrigerant, and for other uses. By subjecting the segregated vaporous component to the refrigerating action of an expanding liquid in a refrigerating device, the temperature of the vapor may be reduced to a degree sufficient to condense the same; and the liquefied mixture may then be withdrawn in liquid form, and under pressure, and packaged for use in suitable containers such, for instance, in steel cylinders or tanks.

The expanded refrigerant is subjected to a recovery treatment including absorption in a petroleum liquid. The mixture is then distilled and the recovered refrigerant is returned to the system.

An example of the process may be better understood by reference to the apparatus disclosed in the accompanying drawing in which 1 indicates a rectifying column having a supply pipe 2 which preferably enters the rectifying column approximately intermediate of its height. Adequate heat is generated for raising the temperature of the contents of the column 1 to a degree which, when coordinated with predetermined pressures in accordance with known practice, accomplishes the initial segregation of the liquid and vaporous components. It will be understood that an internal pressure is maintained in the rectifying column by the gases generated therein. The heat may be generated by any known means and the illustrated embodiment includes a preheater 3 having a heating coil 4, a steam inlet pipe 5 and a steam return pipe 6. The preheater is connected with the well 7 of the rectifying column 1 by pipe connections 8 and 9.

In the normal operation of the apparatus thus far described, the heavier fractions in ratio to their weight are liquefied and disposed in the column 1 from the bottom to the top thereof. That is to say, the heavier liquids condense in the lower part of the rectifying column 1 from which they are withdrawn through a take off pipe 10, being discharged through a cooler before pressure is relieved in accordance with known practice, and the lighter fractions accumulate in the upper zone of the column.

The lighter volatile components are driven off in vaporous form through the conduit comprising the pipes 11 and 12, by means of which they are conducted to a condenser 13. The condenser 13 is preferably water cooled, and reduces the temperature of the vaporous component passing therethrough to a degree sufficient to liquefy a portion thereof, said liquefied component having a relatively low boiling point and being of itself of such character that upon expansion it acts as a satisfactory refrigerant. A portion of the mixture entering the condenser 13 remains in vaporous form and comprises the lightest fractions reduced from the original mixture. It is ordinarily principally in the form of propane with an admixture of the homologous hydrocarbons such as isobutane, butane and ethane.

The liquid and vaporous mixture from the condenser 13 is conducted to a container 14 by a pipe 15, and the liquid residue is conducted from the tank 14 to a trap comprising the pipes 16, 17 and 18, the pipe 18 being connected at its upper end with a nozzle 19 discharging interiorly of the upper portion of the rectifying column 1. The reflux liquid discharged from the nozzle 19 operates in the rectifying column 1 for washing out all of the fractions to be reclaimed in the initial segregation and comprised in the liquid withdrawn from said rectifying column through the pipe 10, according to known practice.

The vaporous component resulting from the treatment in the condenser 13 is withdrawn from the upper part of the container 14 through a pipe 20 by means of which it is conducted to a refrigerator 21. The separation at this point is a gravity separation, the vapor rising to the top of the container and the liquid flowing to the pipe 16 from the lower zone of the container, as will be readily understood.

The refrigerator 21 may be of any known type comprising expansion coils and a condensing chamber. The refrigerator is cooled by means of the expansion of a part of the liquid which accumulates in the trap formed by the pipes 16—17—18 and is conducted therefrom by a branch pipe 22 leading to the expansion coils of the refrigerator 21. The action of the refrigerator 21 may be controlled so that the temperature of the influent vaporous mixture entering the refrigerator from the pipe 20 is reduced below a point at which the fraction thereof that it is desired to recover in liquid form will entirely condense, at the internal pressure in the condensing chamber. It will be understood that the internal pressure in the condensing chambers renders it possible to condense the vapor at the temperature reduction effected by the expansion of the liquid in the expansion coils.

The condensation of the vapor passing through the refrigerator 21 accumulates in the bottom of the condensing chamber of the refrigerator from which it is withdrawn through a take off pipe 23 and discharged into a container 24 which may be a steel container of the usual type for storing and transporting highly volatile liquids. The weight of the contents at the time the steel cylinders are filled may be standardized by filling the cylinders on a scale 25. The take off line 23 may be controlled by a filling valve 26.

In order to regulate the flow through the pipe 20 a valve 27 may be provided therein. The flow of the refrigerant to the refrigerator 21 may be controlled automatically by a thermostatic valve 28, the thermostatic element 29 of which is in the take off line 23. Thus, as determined by the temperature of the liquid discharged from the refrigerator 21, more or less of the refrigerating liquid from the pipe 22 may be admitted to the expansion coils of the refrigerator 21, as may be required to effect condensation.

In order to recover the vapor resulting from the expansion in the expansion coils of the refrigerator 21, the vapor is conducted by a pipe 30 from the refrigerator to an absorber 31. The absorber 31 is preferably in the form of a steel cylinder having an extended internal surface. The absorber 31 contains a quantity of cooled hydrocarbon liquid such, for instance, as petroleum oil. It is desirable that the liquid absorbent utilized as the absorbing agent have a low viscosity and a relatively low molecular weight (preferably 80 to 225).

The absorber 31 is internally cooled by any suitable means such, for instance, as water coils 32 having external connections 33 and 34. The absorber 31 is also preferably provided with a relief valve 35 outwardly operating against a predetermined maximum pressure. The purpose of the valve 35 is to relieve the absorber of insoluble gases such as methane, air, water, vapor, or other accumulated elements that will not absorb in the absorbing agent. The action of the absorber 31 upon the vapor entering through the pipe 30 is to effect a substantially complete absorption of the vapor in the heavy hydrocarbon liquid. It will be understood that the temperature and pressure in the absorber is coordinated to effect a satisfactory degree of absorption of the vapor in the absorbing liquid in the absorber.

The liquid containing the absorbed vapor is conducted under forced pressure by means of a pump 36 to a conduit 37, thence through a heat exchanger 38 and a pipe 39 to the upper part of a still 40, the pipe 39 discharging into the still through an internal nozzle 41. The still 40 is internally heated by any suitable means such, for instance, as a steam coil 42 having a steam inlet and return passage 43 and 44, the passage 44 discharging through a steam trap 45. The still 40 may be in the form of a rectifying column so that a more effective separation of the absorbed vapor and the absorbing liquid may be accomplished by proper balancing of pressure and temperature.

The action of the still 40 is to drive off from the heavier hydrocarbon liquid containing the absorbed gas the vaporous component comprising the fractions substantially corresponding to the mixture that was used as the refrigerant in the refrigerator 21. The segregation into these selected groups is effected by the proper balancing of pressure and temperature, so that this end will be substantially effected by the treatment in the still 40. The residue of the liquid in the still, after the selected vaporous components have been expelled, accumulates in the bottom thereof and the vaporous components are driven off from the top of the still through a conduit 46 through which it may be returned to the system by connecting the pipe 46 into the pipes 11 and 12. The accumulated heavier liquid in the still is withdrawn therefrom through a conduit 47 through which it is conducted to the heat exchanger 38, the heated liquid from the still being initially cooled by the effect of the mixture of lower temperature flowing through the heat exchanger 38 from the pipe 37.

From the heat exchanger 38 the mixture is subjected to a secondary cooling treatment in a cooler 48 to which it is conducted from the heat exchanger 38 by a pipe 49. The cooler 48 is cooled by water or other outside cooling agent and, after treatment in the cooler 48, the liquid is reintroduced into the absorber 31 through a pipe 50 having a nozzle 51 internally disposed in the upper part of the absorber 31.

From the foregoing description of the process it will be understood that the process has particular applicability to the treatment of a starting material substantially of the character of natural gases and petroleum vapors such as casing head gas or the vapors that rise from petroleum oils in storage or from the various refining processes. As is known, such gases include a component that may be maintained as a liquid under normal pressure and temperatures and which is generally known as a natural gas gasoline. The original mixture also includes the light fractions hereinbefore specified and comprising principally propane and lighter fractions with an admixture of the homologous hydrocarbons.

What I claim and desire to secure by Letters Patent is:—

1. That process for treatment of hydrocarbons having substantially the characteristic of natural gas, which consists in splitting the hydrocarbon mixture into a liquid component and a vaporous component by rectification; then condensing a part of said vaporous component to form a secondary liquid component; then expanding said secondary liquid component to effect a cooling action; and subjecting the vaporous component while under pressure to the cooling action of the expansion of said secondary liquid component to condense said last named vaporous component.

2. A continuous process for the treatment of hydrocarbon mixtures substantially of the character of natural gas, which consists in subjecting the hydrocarbon mixture to a rectification treatment under balanced pressures and temperatures to split the mixture into a liquid and a vaporous component; cooling the vaporous component to further split said vaporous component into a secondary liquid component and a vaporous component; then effecting a gravity separation of said last named components; then expanding said last named liquid component; passing the vaporous component within the cooled area resulting from the expansion of said last named liquid component, thereby condensing said last named vaporous component to a liquid state; and then recovering the expanded liquid component in a vaporous state and returning the same to the system.

3. A continuous process for the treatment of hydrocarbon mixtures of the general character of natural gas, which consists in subjecting the hydrocarbon mixture to a rectification treatment under balanced pressures and temperatures to split the mixture into a liquid and a vaporous component; cooling the vaporous component to further split said vaporous component into a secondary liquid component and a vaporous component; then effecting a gravity separation of said last named component; then expanding said last named liquid component; passing the vaporous component within the cooled area without releasing the pressure thereon, thereby condensing the same to a liquid state; and then recovering the expanded liquid component in a vaporous state and returning the same to the system.

4. A continuous process for the treatment of hydrocarbon mixtures responding in composition substantially to natural gas, which consists in subjecting the hydrocarbon mixture to a rectification treatment under balanced pressures and temperatures to split the mixture into a liquid and a vaporous component; cooling the vaporous component to further split said vaporous component into a secondary liquid component and a vaporous component; returning a portion of said condensate as a reflux liquid for the rectification step; withdrawing the vapor resulting from said separation; withdrawing a portion of the condensate and expanding the same; passing the vaporous component within the cooled area of the expanding condensate to liquefy said vaporous component; and then withdrawing the condensated vapor in the form of a liquid from the system.

5. A continuous process for the treatment of a mixed hydrocarbon gas of the character of natural gas, which consists in subjecting the hydrocarbon mixture to a rectification treatment under balanced pressures and temperatures to split the mixture into a liquid component and an overhead vaporous component; cooling the overhead vaporous component to further split the same into a secondary liquid component and a vaporous component; then effecting a gravity separation of said last named component; then expanding said last named liquid component; passing the vaporous component within the cooled area under a sufficient vapor pressure to condense the same at the temperature produced by the expanding of said last named liquid component; and then withdrawing the condensate from the system.

6. A continuous process for the treatment of a mixed hydrocarbon gas of the character of natural gas, which consists in subjecting the starting mixture to a rectification treatment under balanced pressures and temperatures to split the mixture into a liquid component and a vaporous overhead component; cooling the overhead product to further split the same into a secondary liquid component and a vaporous component; then effecting a gravity separation of said last named components; then expanding said last named liquid component; passing the vaporous component within the cooled area under a sufficient vapor pressure to condense the same at the temperature attained by the expansion of said last named liquid component; then withdrawing the condensate from the system; and controlling the temperature of said cooled area by controlling the supply of liquid expanded by the temperature of said last named condensate as it leaves the system.

7. The steps in the herein described process of liquefying light hydrocarbon fractions of a hydrocarbon mixture substantially of the character of natural gas, which consists in withdrawing the vapors from a liquid corresponding to natural gas gasoline separated therefrom by rectification, cooling the vapors to produce a liquid component and a vaporous component, separating the two components by gravity, and thereafter, while maintaining the vaporous component at the pressure of the system, cooling it further by an out of contact evaporation of a part of the liquid component at a lower pressure.

8. The steps in the herein described process of liquefying light hydrocarbon fractions of a hydrocarbon mixture substantially of the character of natural gas, which consists in withdrawing the vapors from a liquid corresponding to natural gas gasoline separated therefrom by rectification, cooling the vapors to produce a liquid component and a vaporous component, separating the two components by gravity, thereafter, while maintaining the vaporous component at the pressure of the system, cooling it further by an out of contact evaporation of a part of the liquid component at a lower pressure, and controlling the extent of condensation of the vaporous component by controlling the amount of the liquid expanded in the cooling step.

9. A continuous process for the treatment of hydrocarbon mixtures corresponding substantially to natural gas which consists in subjecting the starting mixture to a rectification treatment under balanced pressures and temperatures, said pressures being in excess of atmospheric pressure to fractionate the mixture into a liquid and vaporous component, then reducing the temperature of the vaporous component to further fractionate it into a highly volatile gas and into a secondary liquid component, separating the secondary liquid component from the highly volatile component, effecting an out of contact expansion of the liquid component in an area traversed by the vaporous component while the vaporous component remains under the normal pressure in the system whereby the highly volatile vaporous component is condensed, withdrawing the condensate of the vaporous component under pressure, withdrawing the expanded gas resulting from the cooling step, and returning the same to the system.

SAMUEL C. CARNEY.